(12) United States Patent
Commo et al.

(10) Patent No.: US 8,445,004 B2
(45) Date of Patent: May 21, 2013

(54) ADMINISTRATION OF AGENTS MIMICKING DOPACHROME TAUTOMERASE (TRP-2) ACTIVITY FOR PROTECTING HAIR FOLLICLE MELANOCYTES

(75) Inventors: Stephane Commo, Paris (FR); Olivier Gaillard, Forges-les-Bains (FR); Bruno Bernard, Neuilly sur Seine (FR)

(73) Assignee: L'Oreal, Paris (FR)

( * ) Notice: Subject to any disclaimer, the term of this patent is extended or adjusted under 35 U.S.C. 154(b) by 579 days.

(21) Appl. No.: 12/541,398

(22) Filed: Aug. 14, 2009

(65) Prior Publication Data

US 2010/0074929 A1    Mar. 25, 2010

Related U.S. Application Data

(60) Division of application No. 11/009,153, filed on Dec. 13, 2004, now Pat. No. 7,585,514, which is a continuation of application No. PCT/FR03/01729, filed on Jun. 10, 2003.

(60) Provisional application No. 60/389,708, filed on Jun. 19, 2002.

(30) Foreign Application Priority Data

Jun. 11, 2002 (FR) ...................... 02 07137

(51) Int. Cl.
*A61K 8/02* (2006.01)

(52) U.S. Cl.
USPC ........................................................ 424/401

(58) Field of Classification Search
None
See application file for complete search history.

(56) References Cited

U.S. PATENT DOCUMENTS

| | | | | |
|---|---|---|---|---|
| 4,508,706 | A | * | 4/1985 | Pawelek et al. ............ 424/60 |
| 5,223,538 | A | | 6/1993 | Fridovich et al. |
| 5,965,157 | A | | 10/1999 | Li et al. |
| 6,589,948 | B1 | | 7/2003 | Malfroy-Camine et al. |
| 2002/0103216 | A1 | | 8/2002 | Pruche et al. |
| 2002/0183297 | A1 | | 12/2002 | Niazi et al. |
| 2003/0175231 | A1 | | 9/2003 | Gilchrist et al. |

FOREIGN PATENT DOCUMENTS

| | | |
|---|---|---|
| EP | 0 327 345 | 8/1989 |
| EP | 0 545 147 | 6/1993 |
| EP | 0 580 409 | 1/1994 |

OTHER PUBLICATIONS

Redondo et al "Repigmentation of Gray Hair After Thyroid Hormone Treatment" Actas Dermosifiliogr. 2007; 98; pp. 603-610.*
Botchkareva et al "SCF/c-kit signaling is required for cyclic regeneration of the hair pigmentation unit", The FASEB Journal; Mar. 2001, vol. 15, p. 645-658.*
Nishimura "Melanocyte stem cells: a melanocyte reservoir in hair follicles for hair and skin pigmentation", Pigment Cell and Melanoma Research, Jun. 2011; vol. 24, Is. 3, (abstract only 2 pages).*
Rabbani et al "Coordinated Activation of Wnt in Epithelial and Melanocyte Stem Cells Initiates Pigmented Hair Regeneration", Cell, 145, p. 941-944, Jun. 10, 2011.*
Decision of Rejection dated Apr. 17, 2007 issued in corresponding JP Application No. 2004-510737 (with English Translation).
International Search Report dated Jan. 9, 2004 issued in International Application No. PCT/FR2003/01729.
Henke et al. "Superoxide Dismutase Mimics as Future Therapeutics" in Expert Opinion on Therapeutic Patents, 1999, vol. 9, No. 2, pp. 169-180.
Tjalve et al. "Affinity of Putrescine, Spermicide, and Spermine for Pigmented Tissues" in Biochemical and Biophysical Research Communications, 1982, vol. 109, No. 4, pp. 1116-1122.
Declercq et al. "Use of the Synthetic Superoxide Dismutase/Catalase Mimetic EUK-134 to Compensate for Seasonal Antioxidant Deficiency by Reducing Pre-Existing Lipid Peroxides at the Human Skin Surface" International Journal of Cosmetic Science, 2004, vol. 26, pp. 255-263.
Emerit et al. "Protective Effect of Superoxide Dismutase Against Hair Graying in a Mouse Model" Photochemistry and Photobiology, 2004, vol. 80, pp. 579-582.

* cited by examiner

*Primary Examiner* — Bethany Barham
(74) *Attorney, Agent, or Firm* — Buchanan Ingersoll & Rooney PC

(57) ABSTRACT

Agents mimicking DOPAchrome tautomerase activity are administered, notably topically applied, to protect and/or regenerate the melanocytes of hair follicles, to promote the cyclic renewal of the follicular pigmentation unit, to prevent and/or limit and/or arrest the development of canities, and to maintain the natural pigmentation of gray or white head hair and/or body hair.

1 Claim, 3 Drawing Sheets

Figure 1:
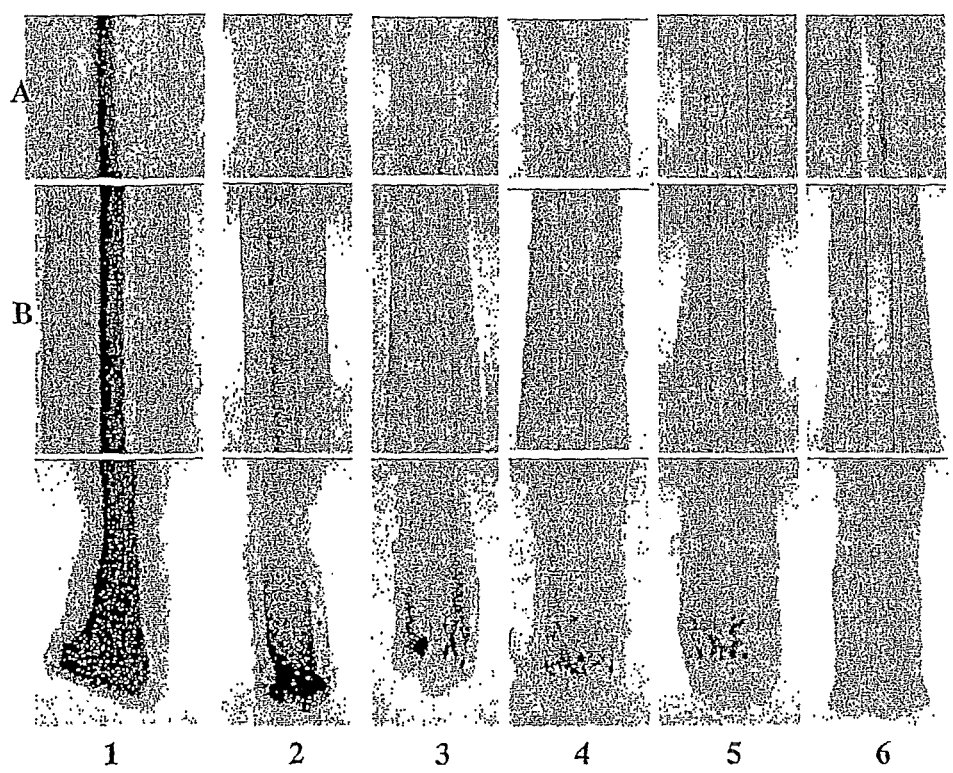

ADMINISTRATION OF AGENTS MIMICKING DOPACHROME TAUTOMERASE (TRP-2) ACTIVITY FOR PROTECTING HAIR FOLLICLE MELANOCYTES

CROSS-REFERENCE TO PRIORITY/PCT/PROVISIONAL APPLICATIONS

This application is a divisional of U.S. application Ser. No. 11/009,153, filed Dec. 13, 2004, which claims priority under 35 U.S.C. §119 of FR 02/07137, filed Jun. 11, 2002, and of provisional application Ser. No. 60/389,708, filed Jun. 19, 2002, and is a continuation of PCT/FR 03/001729, filed Jun. 10, 2003 and designating the United States (published in the French language on Dec. 18, 2003 as WO 03/103616 A3; the title and abstract were also published in English), each hereby expressly incorporated by reference and each assigned to the assignee hereof.

CROSS-REFERENCE TO COMPANION APPLICATION

Application Ser. No. 11/009,364, filed on Dec. 13, 2004 and assigned to the assignee hereof is now abandoned.

BACKGROUND OF THE INVENTION

1. Technical Field of the Invention

The present invention relates to the administration of agents mimicking DOPAchrome tautomerase activity, for protecting the melanocytes of the hair follicle. In particular, the agents mimicking DOPAchrome tautomerase activity combat the disappearance of the melanocytes of the hair follicle by maintaining and/or regenerating the population of active melanocytes of the bulb and of quiescent melanocytes of the upper or top region of the hair follicle.

2. Description of Background and/or Related and/or Prior Art

The hair follicle is a tubular invagination of the epidermis which extends up to the deep layers of the dermis. The bottom part, or hair bulb, itself comprises an invagination in which is the dermal papilla. The bottom part of the bulb is a zone of cellular proliferation where the precursors of the keratinized cells constituting the hair are found. The ascending cells derived from these precursors are gradually keratinized in the top part of the bulb, and this group of keratinized cells will form the hair shaft.

The color of head hair and of body hair depends in particular on the presence in variable quantities and ratios of two groups of melanins: eumelanins (brown and black pigments) and pheomelanins (red and yellow pigments). The pigmentation of head hair and of body hair requires the presence of melanocytes in the bulb of the hair follicle. These melanocytes are in an active state, that is to say that they synthesize melanins. These pigments are transmitted to the keratinocytes intended to form the hair shaft, which will result in the growth of a pigmented head hair or body hair. This structure is called hereinafter "the follicular unit of pigmentation".

In mammals, melanogenesis involves at least three enzymes: tyrosinase, DOPAchrome tautomerase (TRP-2, for Tyrosinase Related Protein 2) and DHICAoxidase (TRP-1, for Tyrosinase Related Protein 1).

Tyrosinase is the enzyme which initiates the biosynthesis of melanins. It is also described as being the enzyme which limits melanogenesis.

TRP-2 catalyzes the tautomerization of DOPAchrome 5,6-dihydroxyindole-2-carboxylic acid (DHICA). In the absence of TRP-2, DOPAchrome undergoes spontaneous decarboxylation to form 5,6-dihydroxyindole (DHI).

DHICA and DHI are both precursors of pigments, TRP-1 oxidizes DHICA molecules to form quinone derivatives (Pawelek J M and Chakraborty A K. The enzymology of melanogenesis. In: Nordlund J J, Boissy R E, Hearing V J, King R A, Ortonne J-P. *The Pigmentary System: Physiology and Pathophysiology*, New York: Oxford University Press; 1998. p. 391-400).

The three enzymes, tyrosinase, TRP-2 and TRP-1, appear to be specifically involved in melanogenesis. Furthermore, the activity of these three enzymes has been described as necessary for the maximum activity of biosynthesis of eumelanins.

The expression of TRP-2 has been observed in the hair of black mice, both in the active melanocytes of the bulb and in the quiescent melanocytes of the outer epithelial sheath. Furthermore, it is known that the DOPAchrome tautomerase activity is increased during the anagen phase in black mice. However, no clear correlation has been established between the expression of TRP-2 and the intensity of the pigmentation (Sturm et al., 1995).

Moreover, TRP-2 has also been described as conferring on the melanocytes expressing it resistance to DNA damaging agents such as cis-diaminedichloroplatinum(II) (Chu et al., 2000 and Pak et al., 2000). These results suggest that TRP-2 might also be involved in a function independent of melanogenesis; the enzyme could play a cytoprotective role.

Head hair and body hair undergo a cycle. This cycle comprises a growth phase (anagen phase), a degenerative phase (catagen phase) and a resting phase (telogen phase) after which a new anagen phase will develop. Because of this hair cycle, and unlike the epidermal pigmentation unit, the follicular pigmentation unit must also be cyclically renewed.

This process was recently described in humans (Commo S. and Bernard B., 2000, *Pigment Cell Res.,* 13:253-259). It has more particularly been shown that during the telogen-anagen transition, a portion of the inactive melanocytes contained in the telogen capsule proliferate, become positioned around the dermal papilla of the nascent bulb and start to express enzymes necessary for the synthesis of melanins: this population of melanocytes corresponds to the active melanocytes of the bulb. In parallel, the other portion of the melanocytes remains inactive in the top region of the hair follicle: this population of melanocytes corresponds to the quiescent melanocytes of the top region of the hair follicle.

These melanogenic enzymes will be expressed in the melanocytes of the bulb during the entire duration of the anagen phase but will no longer be expressed during the catagen and telogen phases. The normal cycle for the melanocytes in the human hair follicle requires the presence of quiescent melanocytes in the top region of the hair follicle, a region otherwise called "reservoir", which will be cyclically activated in order to regenerate the follicular pigmentation unit. This mechanism of cell renewal which participates in maintaining pigmentation is specific to the follicular pigmentation unit; it is not found in the epidermal pigmentation unit.

It is accepted that canities (natural whitening or graying of the hair) is associated with a decrease in melanin in the hair shaft. The cause of this decrease has not been elucidated to date. Several hypotheses have been advanced; it could be linked to a decrease in the melanogenic activity, by analogy with the mechanism of pigmentation of the skin, but also to an impairment in the transfer of melanins or a decrease in the number of melanocytes in the bulb (Tobin and Paus, 2001); and no demonstration in hair pigmentation has to date made it possible to validate either of these hypotheses.

Applicants have now demonstrated two results which validate for the first time the hypothesis according to which canities could be linked to a decrease in the number of active melanocytes in the bulb and a decrease in the number of quiescent melanocytes in the top region of the hair follicle. This premature decrease and/or disappearance of the melanocytes is specific to the hair follicle and does not visibly affect the epidermis.

To date, it was indeed considered that quiescent melanocytes were present in the hair follicles of white hair (Takada et al., 1992, Horikawa et al., 1996, Jenner and Randall 2000).

Also, Applicants have now observed that the progression of canities is associated with a decrease in the number of melanocytes in the hair bulbs which, although in a limited number, synthesize and transfer melanins. Applicants have also observed, unexpectedly and surprisingly, that the population of quiescent melanocytes in the top or upper region of the human hair follicle (also called "reservoir") is also reduced during the canities process, white hair now possessing only a few—or even no—melanocytes, unlike the infundibulum and the epidermis near this white hair. This disappearance affects prematurely and specifically the melanocytes contained in the hair.

It therefore appears necessary to combat the disappearance of the melanocytes of the human hair follicles, a process which affects both the active melanocytes of the bulbs and the quiescent melanocytes of the top region of the hair follicles, in order to combat canities.

Applicants have also observed, unexpectedly, that the enzyme TRP-2 is not expressed in the melanocytes of pigmented (brown, black and red) human hair follicles in Caucasian, Asian and African individuals. This enzyme is not detected either in the active melanocytes of the bulb, or in the quiescent melanocytes of the top region of the human hair follicle whereas it is expressed in the epidermis and the infundibulum of Caucasian, African and Asian individuals. The absence of TRP-2 is associated with the premature disappearance of the melanocytes which do not express it, that is to say the quiescent melanocytes of the top region of the hair follicle and the active melanocytes of the bulb.

SUMMARY OF THE INVENTION

Applicants have therefore demonstrated that TRP-2, which plays a role in melanogenesis (synthesis of melanin) in the epidermal pigmentation unit, plays a different and to date unknown role in the follicular pigmentation unit: the presence of a compound having TRP-2 mimetic activity makes it possible to maintain and/or regenerate the population of quiescent melanocytes of the top region of the hair follicle and the population of active melanocytes of the bulb and thus promotes the cyclic renewal of the follicular unit ensuring the maintenance of the pigmentation of head hair, eyelashes and/or body hair.

Applicants have also identified a means of maintaining and/or regenerating the population of melanocytes of the hair follicle which are responsible for the pigmentation of the hair: indeed, it has been shown that it is possible to mimic TRP-2 activity. Moreover, Applicants have evaluated the cytoprotective activity of agents mimicking TRP-2 under conditions which induce apoptosis and/or senescence of the melanocytes of the hair follicle.

Means for preventing and/or limiting and/or stopping the development of canities and even for maintaining the natural pigmentation of gray or white head hair and/or body hair have now been determined.

Thus, the present invention features administering agents mimicking DOPAchrome tautomerase activity, for protecting the melanocytes of the hair follicle.

DETAILED DESCRIPTION OF BEST MODE AND SPECIFIC/PREFERRED EMBODIMENTS OF THE INVENTION

The expression "agent protecting the melanocytes of the hair follicle" is understood to mean an agent capable of protecting the melanocytes of the hair follicle, in particular against cytotoxic agents responsible for the senescence and/or apoptosis of the melanocytes of the hair follicle. Among the cytotoxic agents, there may be mentioned molecules with genotoxic characters and molecules inducing oxidative stress such as TNF alpha, lipofuscins, TGF beta, the Fas/CD95 ligand, IL1 beta, ferrous and cuprous ions, genotoxic chemical compounds such as cisplatin and oxaloplatin, or compounds such as cyclophosphamide.

The term agent mimicking DOPAchrome tautomerase activity is understood to mean a compound capable of reproducing the effects of DOPAchrome tautomerase on melanocyte metabolism and survival.

In particular, the agent mimicking DOPAchrome tautomerase activity according to the invention is administered to combat the disappearance of the melanocytes of the hair follicle by maintaining and/or by regenerating the population of active melanocytes of the bulb and of the quiescent melanocytes of the top region of the hair follicle.

The agent mimicking DOPAchrome tautomerase activity according to the invention is also intended to promote the cyclic renewal of the follicular pigmentation unit.

In particular, this invention features the use of an agent mimicking DOPAchrome tautomerase activity to prevent and/or limit and/or arrest the development of canities.

The present invention also features the administration of an agent mimicking DOPAchrome tautomerase activity to maintain the natural pigmentation of gray head hair and/or body hair.

The agent mimicking DOPAchrome tautomerase (TRP-2) activity may be selected in particular from among the following compounds:

synthetic molecules mimicking SOD (Métaphore), for example manganese complexes as described in U.S. Pat. Nos. 5,637,578, 5,610,293 and 5,874,421;

antioxidant compounds: such as 5,6,7,8-tetrahydro-1-naphthaneol derivatives, in particular those described in patent EP-0,404,640, oxygenated benzoheterocycle derivatives (see EP-0,685,473), cyclodextrin derivatives (see EP-0,778,287), silicon-containing compounds derived from ascorbic acid (see WO 01/30784), lysine or arginine pyrrolidonecarboxylate (see EP-0,511,118), tert-butyl benzylidenecamphor derivatives (see U.S. Pat. No. 4,952,391), benzylidenecyclanone derivatives (see FR-2,636,531), modified diorganopolysiloxanes (see EP-0,370,868), lipophilic derivatives of benzylidenecamphor (see EP-0,390,681), hydrophilic derivatives of benzylidenecamphor (see EP-0,390,682), benzylcyclanone derivatives (see EP-0,390,683), antioxidant polymers as described in U.S. Pat. No. 4,281,192, combinations of mono- and diesters of cinnamic acid and of vitamin C (see EP-0,664,290), polyamines, such as putrescine, spermidine, spermine, Di-amines, Tri-amines, Tetra-amines; propyl gallate, quercetin, trolox, histidine, tryptophan, methionine, metal chelators (21-aminosteroids), the salen-manganese complex (for example: EUK-8), α-phenyl-tert-butyl nitrol (PBN) (and compounds derived therefrom) or ebselen;

non-antioxidant compounds, such as MIF and its analogs (Macrophage Migration Inhibiting Factor, see Rosengren et al., *Mol. Med.*, 1996, 2(1): 143-9).

The present invention also features compositions for combating canities, comprising, in a cosmetically acceptable medium, at least one agent mimicking DOPAchrome tautomerase (TRP-2) activity as defined above.

The compositions according to the invention comprise a quantity of agent mimicking DOPAchrome tautomerase activity of from 0.001 to 10% by weight per volume, preferably from 0.01 to 5% by weight per volume and still more preferably from 0.1 to 1% by weight per volume.

The compositions according to the invention may be administered, whether regime or regimen, orally or applied to the skin (to any skin area of the body covered with hair) and/or the scalp.

By the oral route, the compositions according to the invention may contain the agent(s) mimicking DOPAchrome tautomerase activity, active compounds in solution in a dietary fluid such as an aqueous or aqueous-alcoholic solution, optionally flavored. They may also be incorporated into an ingestible solid excipient and may be provided for example in the form of granules, pills, tablets or sugar-coated tablets. They can also be placed in solution in a dietary fluid which is itself optionally packaged in ingestible capsules.

Depending on the mode of administration, the compositions of the invention may be provided in any of the galenic forms normally used, particularly in cosmetology. A preferred composition of the invention is a cosmetic composition suitable for topical application to the scalp and/or the skin.

For topical application, the compositions according to the invention may be in particular in the form of an aqueous, aqueous-alcoholic or oily solution or of a lotion- or serum-type dispersion, of emulsions with a liquid or semiliquid consistency of the milk type, which are obtained by dispersing a fatty phase in an aqueous phase (O/W) or conversely (W/O), or of suspensions or emulsions with a soft consistency of the aqueous or anhydrous cream or gel type, or alternatively of microcapsules or microparticles, or of vesicular dispersions of the ionic and/or nonionic type. They may thus be provided in the form of a salve, tincture, cream, ointment, powder, patch, impregnated pad, solution, emulsion or vesicular dispersion, lotion, gel, spray, suspension, shampoo, aerosol or foam. They may be anhydrous or aqueous. They may also be solid preparations constituting cleansing soaps or cakes.

These compositions are prepared according to the customary methods.

The compositions according to the invention may be in particular a composition for hair care, and in particular a shampoo, a hair setting lotion, a treatment lotion, a hair styling cream or gel, a dye (in particular oxidation dye) composition optionally in the form of dyeing shampoos, restructuring lotions for the hair, or a mask.

The cosmetic compositions according to the invention will be preferably a hair cream or lotion, a shampoo or a conditioner.

The quantities of the various constituents of the compositions which can be formulated according to the invention are those conventionally used in the fields considered.

When the composition according to the invention is an emulsion, the proportion of the fatty phase may range from 5% to 80% by weight, preferably from 5% to 50% by weight relative to the total weight of the composition. The oils, waxes, emulsifiers and coemulsifiers contained in the composition in the form of an emulsion are chosen from those conventionally used in the cosmetic field. The emulsifier and coemulsifier are present in the composition in a proportion ranging from 0.3% to 30% by weight, and preferably from 0.5 to 20% by weight relative to the total weight of the composition. The emulsion may additionally contain lipid vesicles.

When the composition according to the invention is a solution or an oily gel, the fatty phase may represent more than 90% of the total weight of the composition.

In one embodiment of the invention, the composition will be such that the agent mimicking DOPAchrome tautomerase activity is encapsulated in a coating such as microspheres, nanospheres, oleosomes or nanocapsules; the coating will be chosen according to the chemical nature of the agent mimicking DOPAchrome tautomerase activity.

By way of example, microspheres may be prepared according to the method described in EP-0,375,520.

Nanospheres may be provided in the form of an aqueous suspension and may be prepared according to the methods described in FR-0,015,686 and FR-0,101,438.

Oleosomes consist of an oil-in-water emulsion consisting of oily globules provided with a lamellar liquid crystal coating dispersed in an aqueous phase (see EP-0,641,557 and EP-0,705,593).

The agent mimicking DOPAchrome tautomerase activity may also be encapsulated into nanocapsules consisting of a lamellar coating obtained from a silicone surfactant (see EP-0,780,115); the nanocapsules may also be prepared based on water-dispersible polysulfonic esters (see FR-0-113,337).

The agent mimicking DOPAchrome tautomerase activity may also be complexed at the surface of cationic oily globules, regardless of their size (see EP-1-010,413, EP-1-010, 414, EP-1-010,415, EP-1-010,416, EP-1-013,338, EP-1-016, 453, EP-1-018,363, EP-1-020,219, EP-1-025,898, EP-1-120, 101 EP-1-120,102, EP-1-129,684, EP-1-160,005 and EP-1-172,077).

The agent mimicking DOPAchrome tautomerase activity may finally be complexed at the surface of nanocapsules or nanoparticles provided with a lamellar coating (see EP-0,447, 318 and EP-0,557,489) and containing a cationic surfactant at the surface (see the references cited above for cationic surfactants).

In particular, a composition will be preferred such as the coating in which the agent mimicking DOPAchrome tautomerase activity has a diameter of less than or equal to 10 µm. When the coating does not form a spherical vesicle, the expression diameter is understood to mean the largest dimension of the vesicle.

In a known manner, the compositions according to the invention may also contain customary adjuvants in the cosmetic field, such as hydrophilic or lipophilic gelling agents, hydrophilic or lipophilic additives, preservatives, antioxidants, solvents, perfumes, fillers, screening agents, odor absorbers and coloring matter. The quantities of these various adjuvants are those conventionally used in the cosmetic field, and are for example from 0.01% to 10% of the total weight of the composition. These adjuvants, depending on their nature, may be introduced into the fatty phase, into the aqueous phase and/or into the lipid spherules.

As oils or waxes which can be used in the invention, there may be mentioned mineral oils (liquid paraffin), vegetable oils (liquid fraction of shea butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. It is also possible to add fatty alcohols and fatty acids (stearic acid) to these oils.

As emulsifiers which can be used in the invention, there may be mentioned for example glyceryl stearate, polysorbate 60 and the PEG-6/PEG-32/glycol stearate mixture sold under the name Tefose® 63 by Gattefosse.

As solvents which can be used in the invention, there may be mentioned lower alcohols, in particular ethanol and isopropanol, propylene glycol.

As hydrophilic gelling agents which can be used in the invention, there may be mentioned carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, there may be mentioned modified clays such as bentones, metal salts of fatty acids such as aluminum stearates and hydrophobic silica, ethylcellulose, polyethylene.

The compositions according to the invention may combine at least one agent mimicking TRP-2 activity with other active agents. Among these active agents, there may be mentioned by way of example:

agents modulating the differentiation and/or proliferation and/or pigmentation of the cells of the skin such as retinol and its esters, vitamin D and its derivatives, estrogens such as estradiol, cAMP modulators such as POMC derivatives, adenosine, or forskolin and its derivatives, prostaglandins and their derivatives, triiodotrionine and its derivatives;

plant extracts such as those from Iridaceae or soybean, which extracts may or may not then contain isoflavones;

extracts of microorganisms;

anti-free radical agents such as α-tocopherol or its esters, superoxide dismutases or its mimetics, certain metal chelators or ascorbic acid and its esters;

antiseborrheics such as certain sulfur amino acids, 13-cis-retinoic acid, cyproterone acetate;

other agents for combating desquamative states of the scalp such as zinc pyrithione, selenium disulfide, climbazole, undecylenic acid, ketoconazole, piroctone olamine (octopirox) and ciclopiroctone (ciclopirox); in particular they may be active agents stimulating the regrowth and/or promoting the slowing down of the loss of hair, and there may be more particularly mentioned without limitation:

nicotinic acid esters, including in particular tocopheryl nicotinate, benzyl nicotinate and $C_1$-$C_6$ alkyl nicotinates such as methyl or hexyl nicotinates;

pyrimidine derivatives, such as 2,4-diamino-6-piperidinopyrimidine 3-oxide or "Minoxidil" described in U.S. Pat. Nos. 4,139,619 and 4,596,812; Aminexil or 2,4-diaminopyrimidine 3-oxide described in WO 96/09048;

agents inhibiting lipoxygenase or inducing cyclooxidase promoting hair regrowth such as those described in European patent application EP-0,648,488;

antibacterial agents such as macrolides, pyranosides and tetracyclines, and in particular erythromycin;

calcium antagonists such as cinnarizine, nimodipine and nifedipine;

hormones such as estriol or analogs, or thyroxin and its salts;

antiandrogenic agents such as oxendolone, spironolactone, diethylstilbestrol and flutamide;

steroidal or nonsteroidal inhibitors of 5-α-reductases such as those described in EP-0,964,852 and EP-1-068,858 or finasteride;

ATP-dependent potassium channel agonists such as cromakalim and nicorandil;

plant extracts with propigmenting activity such as chrysanthemum extracts as described in FR-2,768,343 and the Sanguisorba extracts described in FR-2,782,920 A1.

Preferably, the agent mimicking DOPAchrome tautomerase activity is combined with another active agent chosen from agents for combating desquamative states of the scalp, agents promoting hair regrowth, plant extracts with propigmenting activity.

The present invention also features a method for the cosmetic treatment of canities, during which there is administered or applied to the area to be treated a composition as defined above comprising at least one agent mimicking DOPAchrome tautomerase activity.

This invention also features a cosmetic treatment regime or regimen to maintain the natural pigmentation of gray or white head hair and/or body hair, wherein there is administered or applied to the area to be treated a composition as defined above comprising at least one agent mimicking DOPAchrome tautomerase activity.

Methods for treating canities and pigmentation of grey or white head hair and/or body hair may also entail ingesting a composition comprising at least one agent mimicking DOPAchrome tautomerase activity.

The areas to be treated may be for example and without any limitation the scalp, the eyebrows, the moustache and/or the beard and any area of the skin covered with hair.

More particularly, the methods for the cosmetic treatment of canities and the natural pigmentation of gray or white head hair and/or body hair entail applying a composition comprising at least one agent mimicking DOPAchrome tautomerase activity selected from among:

synthetic molecules mimicking SOD (Métaphore), for example manganese complexes as described in U.S. Pat. Nos. 5,637,578, 5,610,293 and 5,874,421;

antioxidant compounds: such as 5,6,7,8-tetrahydro-1-naphthaneol derivatives, in particular those described in EP-0,404,640, oxygenated benzoheterocycle derivatives (see EP-0,685,473), cyclodextrin derivatives (see EP-0,778,287), silicon-containing compounds derived from ascorbic acid (see WO 01/30784), lysine or arginine pyrrolidonecarboxylate (see EP-0,511,118), tert-butyl benzylidenecamphor derivatives (see U.S. Pat. No. 4,952,391), benzylidencyclanone (see FR-2,636,531), modified diorganopolysiloxanes (see EP-0,370,868), lipophilic derivatives of benzylidencamphor (see EP-0,390,681), hydrophilic derivatives of benzylidenecamphor (see EP-0,390,682), benzylcyclanone derivatives (see EP-0,390,683), antioxidant polymers as described in U.S. Pat. No. 4,281,192, combinations of mono- and diesters of cinnamic acid and of vitamin C (see EP-0,664, 290), polyamines, such as putrescine, spermidine, spermine, Di-amines, Tri-amines, Tetra-amines; propyl gallate, quercetin, trolox, histidine, tryptophan, methionine, metal chelators (21-aminosteroids), the salen-manganese complex (for example: EUK-8), α-phenyl-tert-butyl nitrol (PBN) (and compounds derived therefrom) or ebselen;

non-antioxidant compounds, such as MIF and its analogs (Macrophage Migration Inhibiting Factor, see Rosengren et al., *Mol. Med.*, 1996, 2(1): 143-9).

The methods of cosmetic treatment for combating canities and/or for maintaining the natural pigmentation of gray or white head hair and/or body hair may for example entail applying the composition to head hair and the scalp, in the evening, keeping the composition overnight and optionally shampooing in the morning or washing the hair with this composition and again leaving in contact a few minutes before rinsing. The compositions in accordance with the invention proved to be particularly advantageous when applied in the form of a hair lotion, optionally to be rinsed off or even in the form of a shampoo.

The present invention also features a method for identifying an agent mimicking DOPAchrome tautomerase activity, by determining the capacity of a compound to reduce the induction of cell death in melanocytes not expressing DOPAchrome tautomerase with reference to a population of melanocytes which express DOPAchrome tautomerase, the method comprising the following steps:

a—culturing a population of melanocytes;

b—separating into two populations the population of melanocytes obtained at the end of step (a), called Mel-A and Mel-B respectively, culturing Mel-A in a medium A where the melanocytes express little or no DOPAchrome tautomerase and Mel-B in a medium B containing at least one factor promoting the expression of DOPAchrome tautomerase;

c—exposing the Mel-A population to a condition inducing apoptosis or senescence in culture in the presence (Mel-A(+) population) or in the absence (Mel-A(−) population) of a compound for which it is desired to test the DOPAchrome tautomerase mimicking activity;

d—exposing the Mel-B population to a condition inducing apoptosis or senescence in culture identical to the condition chosen in step (c) in the absence of the compound for which it is desired to test the DOPAchrome tautomerase activity;

e—comparing the apoptotic or senescent responses of the Mel-A(+) population with Mel-A(−) and of Mel-A(+) with Mel-B;

f—selecting the compounds for which the response is such that the cytotoxicity observed in the Mel-A(+) trial is lower than that observed in the Mel-A(−) trial, and the cytotoxicity observed in the Mel-A(+) trial is close to that observed in the Mel-B trial.

In a particular embodiment according to the invention, the melanocytes are cultured in step (a) in M2 medium (PromoCell, Heidelberg, D). The culturing in step (a) may be carried out according to various modalities:

in a monolayer culture system where the cells are inoculated directly on the plastic;

the cells may also be inoculated on one or more extracellular matrix compounds such as collagen, elastin, fibronectin, laminin;

the cells may be cultured in a three-dimensional system, such as a dissected hair, an uprooted hair, a skin reconstructed in vitro.

This step (a) is preferably carried out for a period of between 2 and 18 hours which is necessary for adhesion of the cells.

To carry out the next steps, the culture medium in step (a) is then replaced with a medium appropriate for the test:

for step (b), this is:

for the population of Mel-A melanocytes, a medium not promoting the expression of TRP-2 or a medium containing a factor repressing the expression of DOPAchrome tautomerase for the Mel-A population, it being possible for this factor to be a factor neutralizing the messenger RNAs encoding TRP2 (antisense method, siRNA) with the aid of appropriate nucleotide sequences;

for the population of Mel-B melanocytes of a medium promoting the expression of TRP-2, this medium may also contain a factor inducing the expression of DOPAchrome tautomerase. For example, this factor may be chosen from: hexamethylene bisacetamide (HMBA), glycyrrhizin, diethylstilbestrol, estradiol, kaempferol, forskolin.

The expression of TRP2 may also be obtained after transfecting the coding region of the human gene for TRP-2 (for example as described in genebank No. S69231, No. NM_001922, No. AJ000503) in any appropriate factor (example: pcDNA© Vector, invitrogen, Groningen, CH, N). In this case, the test may be carried out on melanocytes or on any other type of mammalian cells (example: fibroblasts, keratinocytes).

According to a particular embodiment, there will be used in step (b), for the population of Mel-A melanocytes, a medium containing a factor neutralizing the messenger RNAs encoding TRP2 (antisense method, siRNA) with the aid of appropriate nucleotide sequences.

As double-stranded oligonucleotide capable of causing the extinction of the messenger RNA encoding TRP2, it will be possible to use the following 3 nucleotide sequences (positions 838, 1589 and 2164 respectively of the gene encoding TRP2).

The sequences SEQ ID with uneven numbers correspond to the antisense 5' strand; the sequences SEQ ID with even numbers correspond to the sense 5' strand.

```
838
SEQ ID No. 1: 5'-AACATCCATTCCTTGAGTCCTCCTGTCTC-3'

SEQ ID No. 2: 5'-AAAGGACTCAAGGAATGGATGCCTGTCTC-3'

1589
SEQ ID No. 3: 5'-AAGTGATGAGCCTTCATAATTCCTGTCTC-3'

SEQ ID No. 4: 5'-AAAATTATGAAGGCTCATCACCCTGTCTC-3'

2164
SEQ ID No. 5: 5'-AATCCTCACTGTTCCTTCTTGCCTGTCTC-3'

SEQ ID No. 6: 5'-AACAAGAAGGAACAGTGAGGACCTGTCTC-3
```

The functionality of these SiRNA sequences, as specific inhibitors of TRP2, is verified by Western blot measurement of the extinction of the expression of TRP2 in melanocytes in the presence of these SiRNAs in duplex form (antisense strand and sense strand).

To carry out steps (c) and (d), the Mel-A and Mel-B populations are exposed to a condition inducing apoptosis or senescence in culture; this may be for example a proapoptotic factor (TNF α), the absence of a survival factor (IGF-1), a treatment with cisplatin (Pak B. J. et al., 2000, *Melanoma Res.*, 10: 499-505) or oxaliplatin, a toxic agent (cyclophosphamide), an oxidative stress ($H_2O_2$, diethyl maleate) (see Vaux D. L. & Strasser A., 1996, *Proc. Natl. Acad. Sci.*, 93: 2239-2244).

To carry out step (e), it will be possible to use the following methods for visualizing apoptosis or senescence:

the apoptotic response may be determined by any method which makes it possible to visualize cellular apoptosis, for example identification of fragmentation of DNA after agarose gel electrophoresis, labeling of DNA fragments by the "TUNEL" method (Gavrieli Y et al., *J. Cell Biol.*, 1992; 119: 493-501), visualization of anexin V (ApoAlert Annexin V Apoptosis Kit (1996) CLONTECHniques X1(3): 9-11 (BD Biosciences, Belgium)), measurement of caspase activity (ApoAlert Caspase Assay Kit (BD Biosciences, Belgium). In particular, apoptosis may be quantified with the aid of the "Cell Death Detection ELISA plus" kit used according to the protocol given by the supplier (Roche 1 774 425).

the senescent response may be determined by any method which makes it possible to visualize cellular senescence, for example determination of shortening of the telomers, measurement of telomerase activity (TRAPeze kit, Intergen), determination of the reduction in the cyclin E level, determination of the reduction in the phosphorylated P105 Rb protein level (Bandyopadhyay D et al., *Experimental Gerontology*, 2001; 36; 1265-1275), measurement of the beta-galactosidase activity (Dimri G P et al., *PNAS*, 1995; 92; 9363-9367).

This invention also features the use of an agent mimicking DOPAchrome tautomerase activity capable of being identified by the method described above in a method of cosmetic treatment to prevent and/or limit and/or arrest the development of canities and/or to maintain the natural pigmentation of gray or white head hair and/or body hair.

The present invention lastly features the use of an agent mimicking DOPAchrome tautomerase activity capable of being identified by the method described above for the preparation of a cosmetic composition intended to prevent and/or limit and/or arrest the development of canities and/or to maintain the natural pigmentation of gray or white head hair and/or body hair.

Too, this invention features a method for evaluating the cytoprotective activity of an agent mimicking DOPAchrome tautomerase activity capable of being identified by the method described above, comprising the following steps:

a—culturing a population of melanocytes in a medium limiting the expression of TRP-2 to a low basal expression;

b—adding a compound mimicking DOPAchrome tautomerase activity to the culture medium;

c—exposing the cells to a condition inducing apoptosis or senescence;

d—measuring the cytotoxicity;

e—selecting the compounds mimicking DOPAchrome tautomerase activity with a cytoprotective effect.

In a particular embodiment, the cell cultures are carried out in an incubator, at 37° C., 5% $CO_2$.

In particular, step (a) may be carried out according to the following protocol: the melanocytes are inoculated at D0 with M2 medium (PromoCell, Heidelberg, D). After a period necessary for adhesion of the cells of between 2 and 18 hours, the medium is replaced with a medium in which the melanocytes express little or no TRP-2 (low basal expression): DMEM: F12 (Gibco BRL-42400-044), Ultroser G (Gibco BRL-15950-017) 0.5%, PC-1 (BioWhittaker 344022) 0.5%, bFGF (Pepro Tech Inc 100-18B) 5 ng/ml, heparin (Sigma H-3149) 75 ng/ml, 1% antibiotics, 1% glutamine. The cells are maintained in this culture medium for a period of between 12 and 72 hours necessary for decreasing the expression of TRP-2.

Step (b) may be carried out according to the following protocol: the melanocytes are treated in culture with the compound mimicking DOPAchrome tautomerase activity.

Step (c) may be carried out for example according to the following protocol: the cells are treated with cisplatin (for example between 5 and 50 μM) in the culture medium for a period necessary for the induction of apoptosis; this period is generally between 12 and 24 hours.

Step (d) may be carried out for example according to the following protocol: the cytotoxicity may be measured with the aid of the "Cell Proliferation Kit II (XTT)" kit used according to the protocol given by the supplier (Roche 1-465-015). Apoptosis may be quantified with the aid of the "Cell Death Detection ELISA plus" kit, used according to the protocol given by the supplier (Roche 1 774 425).

DESCRIPTION OF THE FIGURES OF DRAWING

FIG. 1: this figure groups together various photographs representing the distribution of melanocytes in the hair follicle during the anagen phase visualized under a microscope.

Legend:

(A) is a series of images of the outer epithelial sheath magnified 40 times, (B) is a series of images of the outer epithelial sheath (centered on the shaft) magnified 20 times and (C) is a series of images of the bulb magnified 20 times.

(1) represents a very dark hair, (2) a moderately pigmented hair, (3) to (5) hairs of different shades of gray and (6) a white hair.

Figure 2:
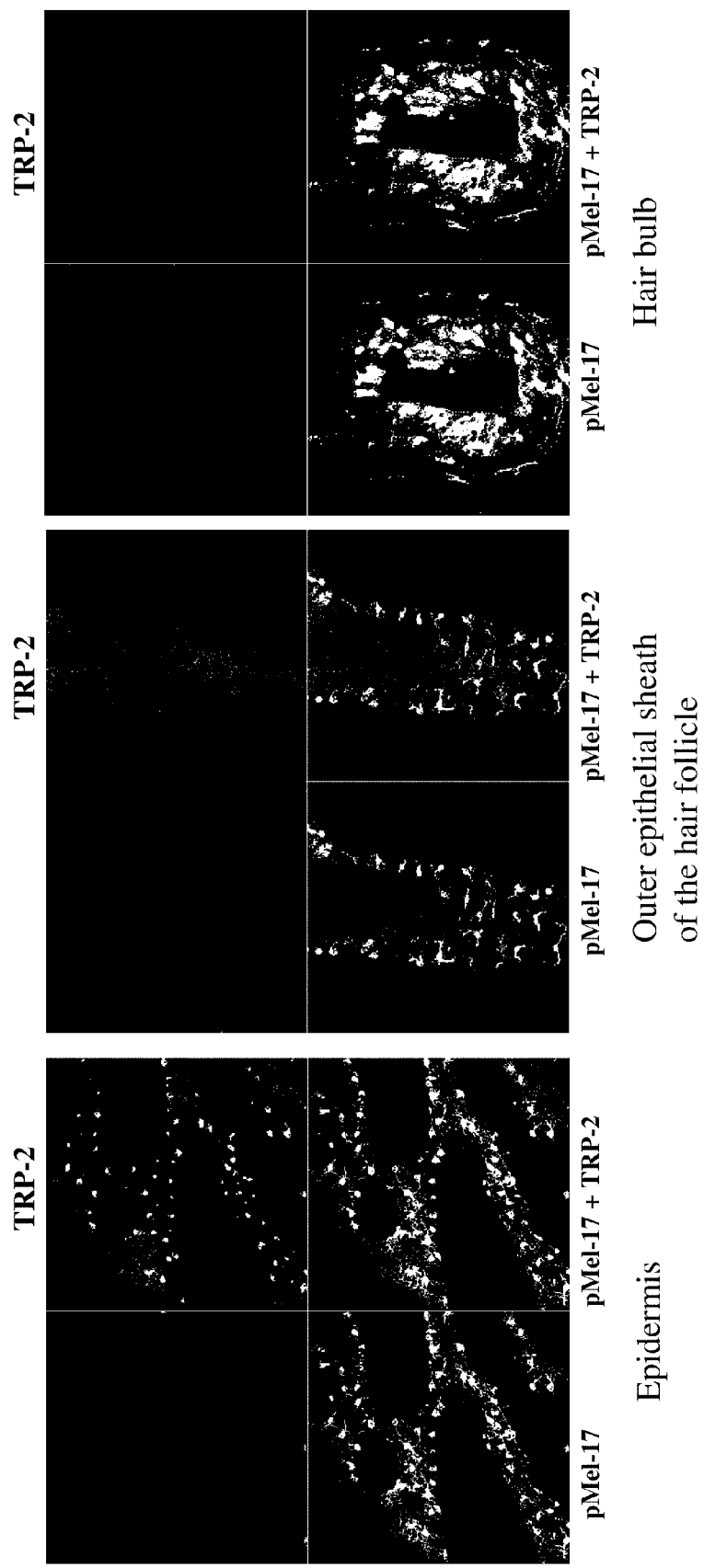

FIG. 2: these photographs make it possible to visualize the expression of TRP-2 in the melanocytes of the epidermis and of the hair (outer epithelial sheath and hair bulb).

Immunohistological study analyzed by confocal laser microscopy.

Figure 3:
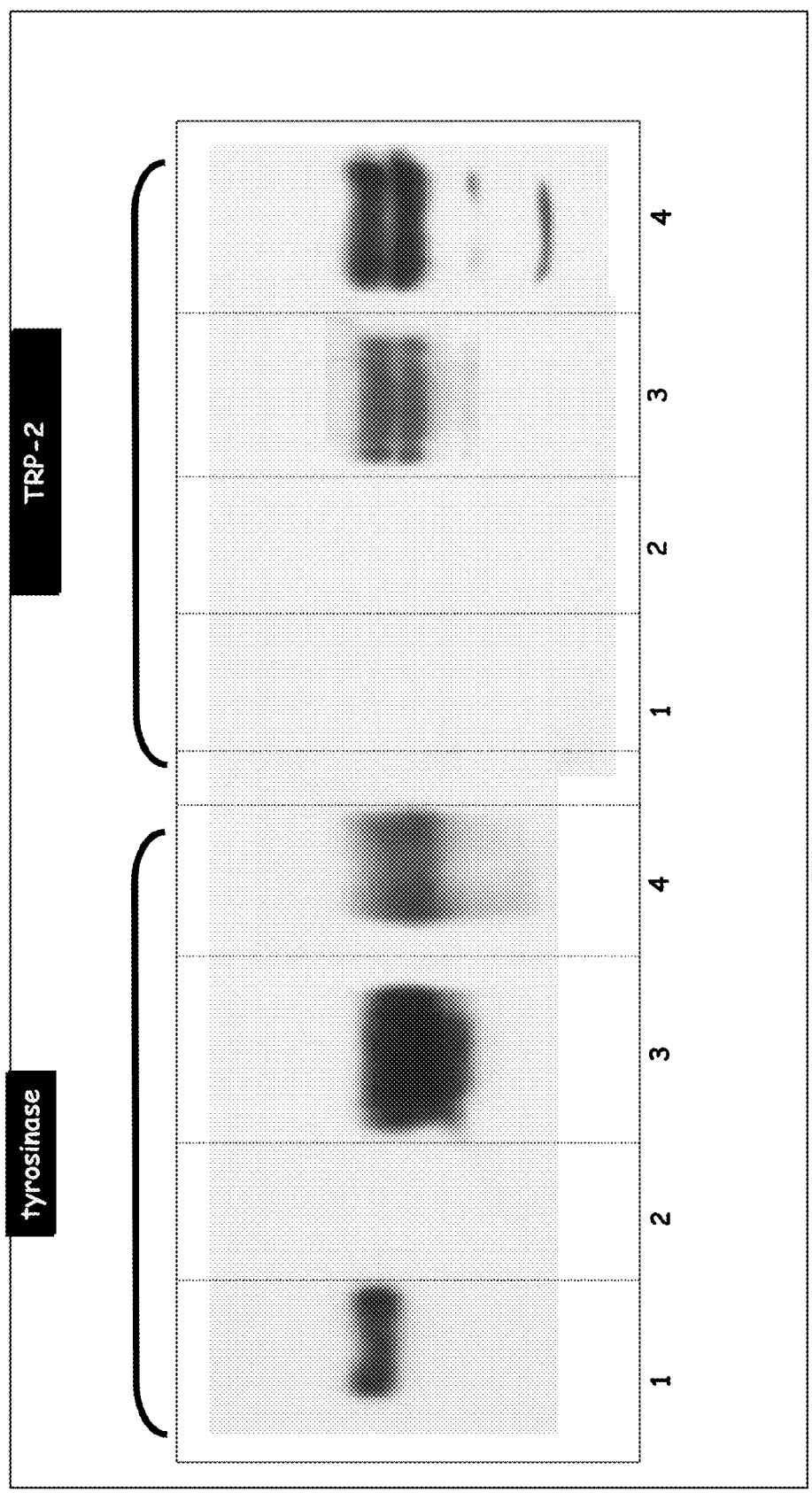

FIG. 3: these photographs represent the results obtained after carrying out Western blotting trials described in example 2B.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

An Immunohistochemical Visualization of the Melanocytes in the Hair Follicles at Various Stages of Whitening, by Labeling the pMel-17 Protein More than 120 hair follicles isolated from biopsies obtained from 8 donors aged from 49 to 71 years were studied.

A—Protocol for Isolating the Whole Hair Follicles: (Commo S and Bernard B A, *Pigment Cell Res.*, 2000; 13:253-259)

Fragments of biopsy are incubated in dispase (2.4 U/ml, Boehringer Mannheim, D) overnight at +04° C. The hair strands are then isolated with the aid of tweezers under binoculars.

B—Immunolabeling Protocol on Whole Hair Follicles: (Commo S and Bernard B A Pigment Cell Res 2000; 13:253-259)

Whole hair strands are fixed in ethanol at −20° C. for 10 minutes. Each step of the fixing and labeling procedures is followed by washings in phosphate buffer (pH 7.4 (PBS))-Tween 20 0.05%. Unless otherwise stated, all the steps are performed at room temperature. The endogenous peroxidases in the sample are neutralized by incubating the sample in a 0.1% hydrogen peroxide solution for 10 minutes. To block the nonspecific binding sites, the sample is incubated with 1% skimmed milk for 15 minutes. The primary antibody (Ab) NK1-beteb specifically recognizing the protein pMel-17 (Monosan, Paris, F) is diluted 1/40 in PBS-Tween 0.05%, containing 10% normal serum (X0907, DAKO, Trappes, F). The primary Ab is incubated for 18 hours on the hair strands at +04° C. The secondary Ab coupled to biotin (E-433, DAKO, Trappes, F) is diluted 1/400 and incubated for 30 minutes. The hair is then incubated in the presence of streptavidin-biotin-peroxidase (K-0377, DAKO, Trappes, F), and finally the immunolabeling is visualized in the presence of 3-amino-9-ethylcarbazole (AEC) (AEC Kit-101, Sigma, Saint Quentin Fallavier, F).

By comparing the images (B1) to (B5) of FIG. 1, it is observed that the decrease in the pigmentation of the hair is associated with a decrease in melanin in the bulb and with a decrease in the melanocytes in the bulb (see C1 to C5). White hair whose shaft lacks melanin (B6) does not contain melanocyte in the bulb (C6). Gray and white hair contain a variable quantity of melanocytes in the top part of the outer epithelial sheath, it being possible for this quantity to even be zero in the case of white hair (A3 to 6) unlike pigmented hair (A1 and 2).

EXAMPLE 2

Demonstration of the Differential Expression of DOPAchrome Tautomerase in the Melanocytes of Hair Follicles and of the Epidermis in Caucasian Individuals A—Immunohistological Study Analyzed by Confocal Laser Microscopy:

A.1—Production of Frozen Sections of Hair Follicle: (Commo S and Bernard B A, *Pigment Cell Res.*, 2000; 13:253-259)

A fragment of scalp biopsy containing hair follicles is embedded in tissue-Tek-OCT (Miles, Naperville, Ill., USA) and then frozen in dry ice. The frozen biopsy is then sectioned (7 µm) with the aid of a cryostat (CM3050, Leica, Rueil-Malmaison, F).

A.2—Protocol for Isolating Whole Hair Follicles and Epithelial Fragments of Skin: (Commo S and Bernard B A, *Pigment Cell Res.*, 2000; 13:253-259)

Fragments of biopsy are incubated in dispase (2.4 U/ml, Boehringer Mannheim, D) overnight at +04° C. The epithelial compartment is separated from the dermis with the aid of tweezers under binoculars. The epithelial structures are then microdissected in order to separate the hair follicles and the epidermis, and then sorted.

A.3—Immunolabeling Protocol on Whole Hair Follicle, Skin Fragment and Frozen Section:

Whole hair strands, epithelial fragments of skin and frozen sections are fixed in ethanol at −20° C. for 10 minutes. Each step of the fixing and labeling procedures is followed by washings in phosphate buffer (pH 7.4 (PBS))-Tween 20 0.05%. Unless otherwise stated, all the steps are performed at room temperature. The endogenous peroxidases in the sample are neutralized by incubating the sample in a 0.1% hydrogen peroxide solution for 10 minutes. To block the nonspecific binding sites, the sample is incubated with 1% skimmed milk for 15 minutes. The primary antibodies (Ab) are diluted in PBS-Tween 0.05%, containing 10% of normal serum (X0907, DAKO, Trappes, F). The primary Ab's NK1-beteb specifically recognizing the protein pMel-17 (1/40, Monosan, Paris, F), and αPEP8h (1/2000, Dr V J Hearing, NIH, Bethesda, Md., USA) specifically recognizing the human protein TRP-2 (Virador et al., 2001) are simultaneously incubated for 18 hours at +04° C. on whole hair strands and epithelial fragments of skin, and for 30 minutes at room temperature on frozen sections. The goat secondary Ab directed against the immunoglobulins (Ig) G2b coupled to Cy3 (M32410, TEBU, le Perray en Yveline, F) is diluted 1/80, and the secondary Ab directed against the Igs coupled to Cy5 (111-175-144, Jackson Immunoresearch Lab. Inc. West Grove, Pa., USA) is diluted 1/500 and they are simultaneously incubated for 30 minutes with the samples. The immunolabelings are analyzed by confocal laser microscopy (LSM510, Carl Zeiss, Oberkochen, D).

Conclusion of the observations: in FIG. 2, the presence of TRP-2 in the melanocytes of the epidermis is observed; on the other hand, this enzyme is not expressed either in the melanocytes of the epithelial sheath of the hair follicle, or in the melanocytes of the hair bulb.

B—Biochemical Study by Western Blot Analysis:

B.1—Protocol for Extraction of Protein from Human Hair Follicles and from Melanocytes: (Commo S et al., *Differentiation*, 2000; 66:157-164)

protein extraction from hair follicles: the hair follicles are isolated after treatment of scalp biopsies with dispase (2.4 U/ml, Boehringer Mannheim, D) overnight at +04° C. After isolation, the hair follicles are microdissected in order to isolate the hair bulb part. 80 hair bulbs thus isolated are placed in an appropriate lysis buffer for protein extraction and Western blot analysis.

protein extraction from a culture of melanocytes: the melanocytes cultured in M2 medium (PromoCell, Heidelberg, D) are lyzed with the same appropriate lysis buffer for protein extraction and analyzed by Western blotting.

The Western blotting (see protocol in Maniatis et al.,) is carried out with the following antibodies: αPEP8h, polyclonal antibody specific for human TRP-2 provided by Dr V J Hearing (NIH, Bethesda, USA), and T311, monoclonal antibody specific for human tyrosinase (Novocastra, Newcastle, UK).

It is observed (FIG. 3) that tyrosinase is detected in the extracts of hair bulb. The enzyme is not detected in the extracts of outer epithelial sheath. The expression of tyrosinase is regulated. This enzyme is not or is little expressed in inactive melanocytes (not producing melanin); that is the case of the melanocytes contained in the interfollicular scalp of a Caucasian individual.

Moreover, DOPAchrome tautomerase (TRP-2) is not detected either in the bulb extracts or in the outer epithelial sheath extracts. The expression of TRP-2 does not follow that of tyrosinase and the induction of melanogenesis; it is not expressed in the active melanocytes of the hair bulbs.

EXAMPLE 3

Compositions

Hair Lotion:

| | |
|---|---:|
| Agent mimicking DOPAchrome tautomerase activity | 0.5 g |
| Propylene glycol | 20 g |
| Ethanol, 95% | 30 g |
| Water | qs 100 g |

This lotion is applied daily to the areas to be treated and preferably to the entire scalp for at least 10 days and preferably 1 to 2 months. A decrease in the appearance of white or gray hair and a repigmentation of gray hair are then observed.

Treatment Shampoo:

| | |
|---|---:|
| Agent mimicking DOPAchrome tautomerase activity | 1.5 g |
| Polyglyceryl 3-hydroxyaryl ether | 26 g |
| Hydroxypropylcellulose sold under the name Klucell G by Hercules | 2 g |
| Preservatives | qs |
| Ethanol, 95% | 50 g |
| Water | qs 100 g |

This shampoo is used at each washing with a leave-in time of about one minute. Prolonged use, of the order of two months, leads to the gradual repigmentation of gray hair.

This shampoo may also be used preventively in order to delay whitening of the hair.

Treatment Gel:

| | |
|---|---|
| Agent mimicking DOPAchrome tautomerase activity | 0.75 g |
| *Eucalyptus* essential oils | 1 g |
| Econozole | 0.2 g |
| Lauryl polyglyceryl 6 cetearyl glycoether | 1.9 g |
| Preservatives | qs |
| Carbopol 934P sold by B F Goodrich Corporation | 0.3 g |
| Neutralizing agent | qs pH 7 |
| Water | qs 100 g |

This gel is applied to the areas to be treated twice a day (morning and evening) with a final massage. After three months of application, repigmentation of body hair or head hair of the treated area is observed.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for combating the disappearance of the melanocytes of hair follicles by maintaining and/or by regenerating the population of active melanocytes of the bulbs and of the quiescent melanocytes of the upper region of hair follicles, comprising topical administeration of EUK-8, 21-aminosteroids, or putrescine to an individual in need of such treatment, for such period of time as required to elicit the desired effect, a thus effective amount of at least one active agent mimicking DOPAchrome tautomerase activity selected from the group consisting of EUK-8, 21-aminsteroids or putrescine.

* * * * *

SEQUENCE LISTING

```
<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: oligonucleotide capable of causing the
      extinction of the messenger RNA encoding TRP2

<400> SEQUENCE: 1
aacatccatt ccttgagtcc tcctgtctc                                          29

<210> SEQ ID NO 2
<211> LENGTH: 29
<212> TYPE: DNA
<213> ORGANISM: Artificial Sequence
<220> FEATURE:
<223> OTHER INFORMATION: oligonucleotide capable of causing the
      extinction of the messenger RNA encoding TRP2

<400> SEQUENCE: 2
aaaggactca aggaatggat gcctgtctc                                          29

<210> SEQ ID NO 3
<211> LENGTH: 29
<212> TYPE: DNA
<213> ORGANISM: Artificial Sequence
<220> FEATURE:
<223> OTHER INFORMATION: oligonucleotide capable of causing the
      extinction of the messenger RNA encoding TRP2

<400> SEQUENCE: 3
aagtgatgag ccttcataat tcctgtctc                                          29

<210> SEQ ID NO 4
<211> LENGTH: 29
<212> TYPE: DNA
<213> ORGANISM: Artificial Sequence
<220> FEATURE:
<223> OTHER INFORMATION: oligonucleotide capable of causing the
      extinction of the messenger RNA encoding TRP2

<400> SEQUENCE: 4
aaaattatga aggctcatca ccctgtctc                                          29

<210> SEQ ID NO 5
<211> LENGTH: 29
<212> TYPE: DNA
<213> ORGANISM: Artificial Sequence
<220> FEATURE:
```

-continued

```
<223> OTHER INFORMATION: oligonucleotide capable of causing the
      extinction of the messenger RNA encoding TRP2

<400> SEQUENCE: 5
aatcctcact gttccttctt gcctgtctc                                29

<210> SEQ ID NO 6
<211> LENGTH: 29
<212> TYPE: DNA
<213> ORGANISM: Artificial Sequence
<220> FEATURE:
<223> OTHER INFORMATION: oligonucleotide capable of causing the
      extinction of the messenger RNA encoding TRP2

<400> SEQUENCE: 6
aacaagaagg aacagtgagg acctgtctc                                29
```